US004001785B2

United States Statutory Invention Registration [19]

[11] Reg. Number: H1785

Theodoridis

[45] Published: Feb. 2, 1999

[54] HERBICIDAL HETEROCYCLYL-SPIROBICYCLIC CATECHOLS

[75] Inventor: George Theodoridis, Princeton, N.J.

[73] Assignee: FMC Corporation, Philadelphia, Pa.

[21] Appl. No.: 124,345

[22] Filed: Jul. 23, 1998

Related U.S. Application Data

[60] Provisional application No. 60/058,023, Aug. 29, 1997.

[51] Int. Cl.[6] ..... A01N 41/00

[52] U.S. Cl. ..... 504/243

*Primary Examiner*—Charles T. Jordan
*Assistant Examiner*—Meena Chelliah

[57] ABSTRACT

It has now been found that certain heterocyclyl-spirobicyclic catechols are useful as pre-emergent and post-emergent herbicides. These compounds are represented by formula II:

II

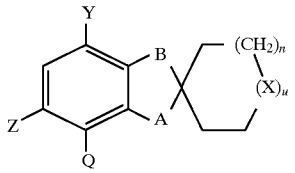

where Q is a 1-substituted-6-trifluoromethyl-2,4 (1H,3H)-pyrimidinedion-3-yl, a 3,4,5,6-tetrahydrophthalimid-1-yl, a 5,6,7,8-tetrahydro-1H,3H-[1,3,4]thiadiazolo[3,4-a]pyridazineimin-1-yl, or a 1,6,8-triazabicyclo[4.3.0]-nonane-7,9-dion-8-yl; and A, B, X, Y, Z, n, u and R are as described in the specification. Preferred are those compounds where A and B are oxygen; Y is chlorine; Z is fluorine; n is 1 when u is 1 or n is 2 when u is 0; and X is oxygen.

15 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

HERBICIDAL HETEROCYCLYL-SPIROBICYCLIC CATECHOLS

This in a provisional application Ser. No. 60/058,023 filed Aug. 29, 1997.

BACKGROUND OF THE INVENTION

This invention relates generally to novel herbicidal compounds and methods for their use in controlling unwanted plant species in agriculture. In particular, it pertains to herbicidal heterocyclyl-spirobicyclic catechols , and more particularly it pertains to heterocyclyl-spirobicyclic catechols where the heterocyclyl portion is a 1-substituted-6-trifluoromethyl-2,4(1H,3H)-pyrimidinedion-3-yl, a 3,4,5,6-tetrahydrophthalimid-1-yl, a 2-[5,6,7,8-tetrahydro-9-oxo-1H,3H-[1,3,4]thiadiazolo[3,4-a]pyridazineiminyl], or a 1,6,8-triazabicyclo[4.3.0]-nonane-7,9-dion-8-yl moiety.

There is a continuing demand for new herbicides. Herbicides are useful for controlling unwanted vegetation which may otherwise cause significant damage to crops such as wheat, corn, soybeans and cotton, to name a few. For crop protection, so-called "selective" herbicides are desired which can control the weeds without damaging the crop. Such crops are said to exhibit tolerance to the herbicide. In certain other situations, it is desirable to use herbicides that provide complete vegetation control such as in areas around railroad tracks and other structures. While many commercial products are available that provide selective or complete vegetation control, the demand exists for new, safe herbicides that are more effective and less costly.

U.S. Pat. No. 5,346,881 (FMC Corp.) describes herbicidally active compounds of the following formula:

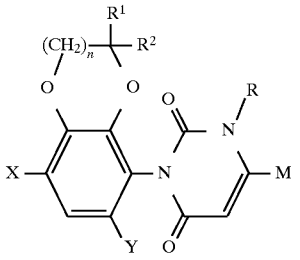

I in which M is fluoroalkyl($C_{1-6}$); R is hydrogen, alkyl($C_{1-6}$), 2-alkynyl($C_{3-6}$), 2-alkenyl($C_{3-6}$), or cyanoalkyl($C_{1-6}$); $R^1$ is hydrogen or alkyl($C_{1-6}$); $R^2$ is hydrogen or alkyl($C_{1-6}$); X is hydrogen, fluorine, chlorine, bromine, cyano, alkyl($C_{1-6}$), or fluoroalkyl($C_{1-6}$); Y is hydrogen, fluorine, chlorine, or bromine, and n is 0or1.

U.S. Pat. No. 5,441,925 (FMC Corp.) describes herbicidally active compounds of formula I above in which M is fluoroalkyl($C_{1-6}$); R is amino; $R^1$ is hydrogen or alkyl($C_{1-6}$); $R^2$ is hydrogen or alkyl($C_{1-6}$); X is hydrogen, fluorine, chlorine, bromine, cyano, alkyl($C_{1-6}$), or fluoroalkyl($C_{1-6}$); Y is hydrogen, fluorine, chlorine, or bromine, and n is 0 or 1.

SUMMARY OF THE INVENTION

It has now been found that certain novel heterocyclyl-spirobicyclic catechols are useful as pre-emergent and post-emergent herbicides. These compounds are represented by formula II:

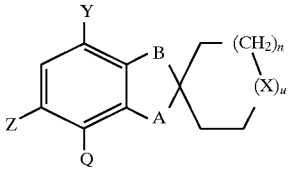

II where Q, A, B, X, Y, Z, n, and u are as described below. Preferred compounds include those in which Q is a 1-substituted-6-trifluoromethyl-2,4(1H,3H)-pyrimidinedion-3-yl; A and B are oxygen; Y and Z are halogen; n is 1 or 2; u is 0 or 1; and X is oxygen.

DETAILED DESCRIPTION OF THE INVENTION

Certain novel heterocyclyl-spirobicyclic catechols are useful as pre-emergent and post-emergent herbicides. These compounds are represented by formula II:

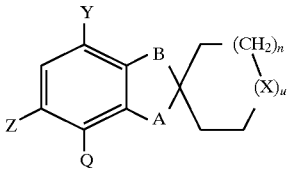

II where Q is

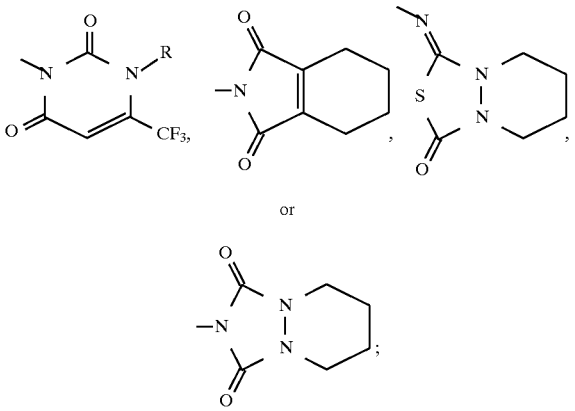

A and B are independently selected from oxygen and sulfur;

u is 0 or 1;

n is 0 to 6;

Y is hydrogen, halogen, cyano, alkyl, or haloalkyl;

Z is hydrogen or halogen;

R is hydrogen, amino, straight or branched chain alkyl, haloalkyl, cyanoalkyl, alkoxyalkyl, arylalkyl, alkoxycarbonylalkyl, alkenyl, alkynyl, or a salt-forming ion; and when u is 1, X is selected from oxygen, sulfur, or -N(alkyl)-.

For Q in formula I the above structural moieties may also be identified by their chemical name as follows:

Q1

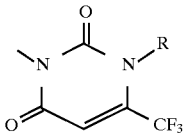

Q2

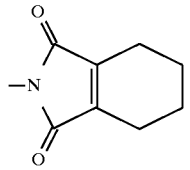

Q3

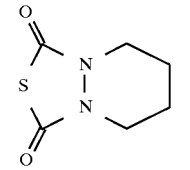

Q4

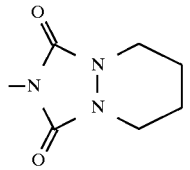

where "Q1" is 1 -substituted-6-trifluoromethyl-2,4(1H,3H) -pyrimidinedion-3-yl, "Q2" is 3,4,5,6-tetrahydrophthalimid-1-yl, "Q3" is 2-[5,6,7,8-tetrahydro-9-oxo-1H,3H-[1,3,4] thiadiazolo[3,4-a]pyridazineiminyl], and "Q4" is 1,6,8-triazabicyclo[4.3.0]-nonane-7,9-dion-8-yl.

One aspect of this invention relates to compounds of formula II where Q is 1-substituted-6-trifluoromethyl-2,4 (1H,3H)-pyrimidinedion-3-yl and A, B, X, Y, Z, n, u, and R are as described above.

Another aspect of this invention relates to compounds of formula II where Q is 3,4,5,6-tetrahydrophthalimid-1-yl and A, B, X, Y, Z, n, and u are as described above.

Another aspect of this invention relates to compounds of formula II where Q is 2-[5,6,7,8-tetrahydro-9-oxo-1H,3H-[1,3,4]thiadiazolo[3,4-a]pyridazineiminyl] and A, B, X, Y, Z, n, and u are as described above.

Another aspect of this invention relates to compounds of formula II where Q is 1,6,8-triazabicyclo[4.3.0]-nonane-7, 9-dion-8-yl and A, B, X, Y, Z, n, and u are as described above.

Preferred are those compounds of formula II where A and B are oxygen; Y and Z are halogen; n is 1 to 6; u is 0 or 1; and X is oxygen.

Particularly preferred are those compounds of formula II where Q is a 1-substituted-6-trifluoromethyl-2,4[1H,3H)-pyrimidinedion-3-yl or 3,4,5,6-tetrahydrophthalimid-1-yl; A and B are oxygen; Y is chlorine; Z is fluorine; X is oxygen; n is 1 when u is 1 or n is 2 when u is 0; and R is methyl or amino.

As used in this specification and unless otherwise indicated the terms "alkyl", "alkenyl", "alkynyl", used alone or as part of a larger moiety includes 1 to 6 carbon atoms. "Halogen" refers to fluorine, bromine, or chlorine. "Salt-forming ion" refers to sodium, potassium, lithium, barium or calcium. "DMF" is N,N-dimethylformamide, "THF" is tetrahydrofuran, and "NCS" is N-chlorosuccinimide.

The heterocyclyl-spirobicyclic catechols of formula II may be prepared by the methods described below or by methods similar to those known to one skilled in the art for similar compounds.

Scheme 1

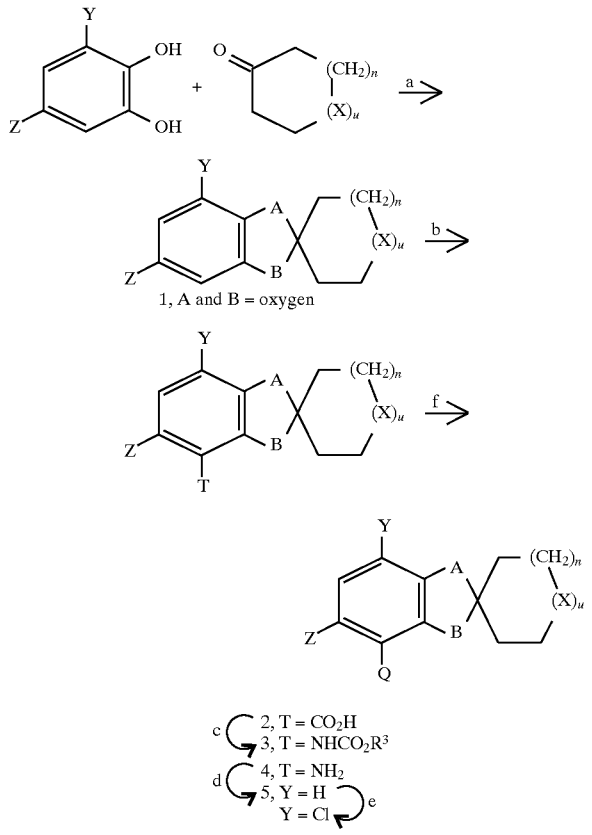

(a) $CH_3C_6H_4SO_3H$, toluene; (b) n-BuLi, $CO_2$, THF; (c) $(PhO)_2PON_3$, $N(C_2H_5)_3$, toluene, $R^3OH$; (d) THF, $Bu_4NF$; (e)NCS, DMF; (f) (1) $ClCO_2CCl_3$, toluene (2) $CF_3C(NH_2) = CHCO_2C_2H_5$, NaH (3) R—X, where X is halogen, $K_2CO_3$ Scheme 1 above illustrates a procedure for preparing compounds of formula II. A similar procedure is taught in U.S. Pat. No. 5,346,881. Procedures for some of the methods that are useful to prepare compounds of this invention are given in the Examples below.

EXAMPLE

Synthesis of 3-[7-chloro-5-fluoro-spiro(1,3-benzodioxole-2-1'-cyclohexan)-4-yl]-1-methyl-6-trifluoromethyl-2,4(1H,3H)-pyrimidinedione (Compound 3)

Step A 5-fluoro-spiro(1,3-benzodioxole-2-1'-cyclohexane)

A stirred solution of 15.0 grams (0.12 mole) of 1,2-dihydroxy-4-fluorobenzene (prepared according to U.S. Pat. No. 5,346,881), 11.5 grams (0.12 mole) of cyclohexanone, and 0.1 gram (0.00053 mole) of paratoluenesulfonic acid in 200 mL of toluene was heated at reflux for 24 hours. The reaction mixture was then analyzed by gas chromatography (GC), which indicated that the reaction was incomplete. The reaction mixture was heated at reflux for an additional 24 hours and the toluene was removed under reduced pressure to yield a residue. The residue was purified by column chromatography on silica gel using hexane, yielding 18.4 grams of title compound, m.p. 58°–62° C. The NMR spectrum was consistent with the proposed structure.

Step B 5-fluoro-spiro(1,3-benzodioxole-2-1'-cyclohexan)-4-ylcarboxylic acid

A stirred solution of 17.9 grams (0.086 mole) of 5-fluoro-spiro(1,3-benzodioxole-2-1'-cyclohexane) in 200 mL of THF was cooled in a dry ice-acetone bath and 36 mL (0.09 mole) of a 2.5 M solution of n-butyllithium in hexanes was added dropwise. The reaction mixture was stirred for 30 minutes after which time a carbon dioxide atmosphere was placed above the reaction mixture. The temperature was allowed to warm to ambient temperature during a 16 hour period while maintaining the carbon dioxide atmosphere. Removal of the solvent under reduced pressure provided a residue to which water was added. The resulting mixture was washed with methylene chloride and acidified using hydrochloric acid. The acidified mixture was extracted with methylene chloride. The methylene chloride extract was washed with water then with an aqueous saturated sodium chloride solution. The organic layer was separated, dried with magnesium sulfate, and filtered. The filtrate was concentrated under reduced pressure, yielding 13.9 grams of title compound, m.p. 139°–141° C. The NMR spectrum was consistent with the proposed structure.

Step C t-butyl N-[5-fluoro-spiro(1,3-benzodioxole-2-1'-cyclohexan)-4-yl]carbamate A stirred solution of 13.4 grams (0.053 mole) of 5-fluoro-spiro(1,3-benzodioxole-2-1'-cyclohexan)4-ylcarboxylic acid, 14.6 grams (0.053 mole) of diphenylphosphoryl azide, and 5.4 grams (0.053 mole) triethylamine in 300 mL of t-butanol was heated to reflux where it stirred for about 18 hours. The t-butanol was then removed under reduced pressure, and the resulting residue was purified by column chromatography on silica gel using hexane and ethyl acetate. The yield of title compound was 7.1 grams, m.p. 118°–120° C. The NMR spectrum was consistent with the proposed structure.

Step D 4-amino-5-fluoro-spiro(1,3-benzodioxole-2-1'-cyclohexane)

A stirred solution of 7.0 grams (0.022 mole) of t-butyl N-[5-fluoro-spiro(1,3-benzodioxole-2-1'-cyclohexan)-4-yl] carbamate in 50 mL of trifluoroacetic acid was cooled in a dry-ice/water bath for two hours. The solvent was then removed providing a residue, to which water was added. The resulting mixture was made basic with an aqueous 10% sodium hydroxide solution and then extracted with ethyl acetate. The ethyl acetate extract was washed with water, then with an aqueous saturated sodium chloride solution. The organic layer was separated, dried with magnesium sulfate, and filtered. The filtrate was concentrated under reduced pressure, yielding 3.6 grams of title compound. The NMR spectrum was consistent with the proposed structure.

Step E 4-amino-7-chloro-5-fluoro-spiro(1,3-benzodioxole-2-1'-cyclohexane)

To a stirred solution of 3.3 grams (0.0148 mole) of 4-amino-5-fluoro-spiro(1,3-benzodioxole-2-1'-cyclohexane) in 50 mL of DMF was added dropwise 2.2 grams (0.0163 mole) of NCS while maintaining the reaction temperature at about 25° C. Upon completion of addition, the reaction mixture was stirred at about 25° C. for about 18 hours. The reaction mixture was then analyzed by GC, which indicated that the reaction was incomplete. A solution of 0.5 gram (0.004 mole) of NCS in sufficient DMF to effect dissolution was added dropwise, and the reaction mixture was stirred at ambient temperature for two hours. Removal of the DMF under reduced pressure provided a residue, to which ethyl acetate was added. The resulting mixture was washed with an aqueous 10% lithium chloride solution, dried with magnesium sulfate, and filtered. The filtrate was concentrated under reduced pressure to yield a residue which was subjected to column chromatography on silica gel using hexane and ethyl acetate, yielding 1.4 grams of title compound. The NMR spectrum was consistent with the proposed structure.

Step F 7-chloro-5-fluoro-spiro(1,3-benzodioxole-2-1'-cyclohexan)isocyanate

To a stirred solution of 1.4 grams (0.0053 mole) of 4-amino-7-chloro-5-fluoro-spiro(1,3-benzodioxole-2-1'-cyclohexane) in 50 mL of toluene was added dropwise 1.1 grams (0.0053 mole) of trichloromethyl chloroformate. Upon completion of addition, the reaction mixture was heated to reflux where it stirred for about 18 hours. The reaction mixture was then concentrated under reduced pressure, yielding 1.5 grams of crude product. The crude product was used in the next step without purification.

Step G

3-[7-chloro-5-fluoro-spiro(1,3-benzodioxole-2-1'-cyclohexan)-4-yl]-6-trifluoromethyl-2,4(1H,3H)-pyrimidinedione A stirred solution of 0.3 gram (0.008 mole) of 60% sodium hydride in 150 mL of THF was cooled to −20° C., and a solution of 1.1 grams (0.0038 mole) of ethyl 3-amino-4,4,4-trifluorocrotonate in 10 mL of THF was added dropwise. The mixture was stirred for ten minutes and then a solution of 1.5 grams (0.0053 mole) of 7-chloro-5-fluoro-spiro(1,3-benzodioxole-2-1'-cyclohexan)isocyanate in sufficient THF to effect dissolution was added dropwise. Upon completion of addition, the reaction mixture was heated to reflux were it stirred for about 18 hours. The THF was then removed and water was added. The resulting solution was washed with diethyl ether, acidified with hydrochloric acid, and extracted with ethyl acetate. The ethyl acetate extract was washed with water then with an aqueous saturated sodium chloride solution. The organic layer was dried with magnesium sulfate and filtered. The filtrate was concentrated under reduced pressure, yielding 0.7 gram of title compound. The NMR spectrum was consistent with the proposed structure.

Step H

Compound 3

A stirred solution of 0.7 gram (0.0017 mole) of 3-[7-chloro-5-fluoro-spiro(1,3-benzodioxole-2-1'-cyclohexan)-4-yl]-6-trifluoromethyl-2,4(1H,3H)-pyrimidinedione, 0.3 gram (0.0025 mole) of potassium carbonate, and 0.3 gram (0.0020 mole) of methyl iodide in 50 mL of THF was heated at reflux for about 18 hours. The reaction was then analyzed by GC, which indicated that the reaction was incomplete. An additional 0.3 gram (0.0025 mole) of potassium carbonate and 0.3 gram (0.0020 mole) of methyl iodide were added. Upon completion of addition, the reaction mixture was stirred at reflux for seven hours. GC analysis again indicated that the reaction was incomplete. An additional 0.3 gram (0.0025 mole) of potassium carbonate and 0.3 gram (0.0020 mole) of methyl iodide were added, and the reaction mixture was heated at reflux for five hours. The THF was then removed under reduced pressure providing a residue to which water was added, and the resulting mixture was extracted with ethyl acetate. The ethyl acetate extract was washed with water, then with an aqueous saturated sodium chloride solution. The organic layer was dried with magnesium sulfate and filtered. The solvent was removed from the filtrate under reduced pressure, yielding a residue which was purified by column chromatography on silica gel using hexane and methylene chloride. The yield of Compound 3 was 0.7 gram. The NMR spectrum was consistent with the proposed structure.

Tables 1 and 2 below show representative compounds of the present invention.

TABLE 1

Herbicidal(2-spirobicyclic heterocyclyl)-substituted heterocycles

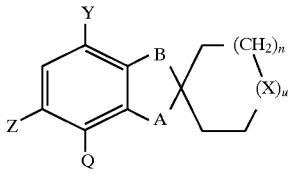

where Q is one of the following:

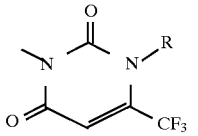

Q1

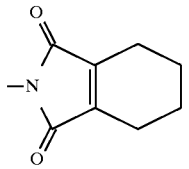

Q2

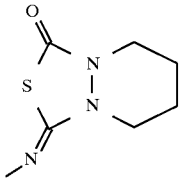

Q3

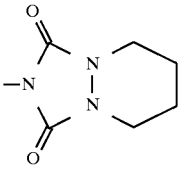

Q4 where A and B are oxygen;

| Cmpd No. | Y | Z | n | u | X | Q | R |
|---|---|---|---|---|---|---|---|
| 1 | Cl | F | 1 | 1 | O | Q1 | $CH_3$ |
| 2 | Cl | F | 1 | 0 | — | Q1 | $CH_3$ |
| 3 | Cl | F | 2 | 1 | — | Q1 | $CH_3$ |
| 4 | Cl | F | 1 | 1 | O | Q1 | H |
| 5 | Cl | F | 1 | 1 | O | Q1 | $C_2H_5$ |
| 6 | Cl | F | 1 | 1 | O | Q1 | n-$C_3H_7$ |
| 7 | Cl | F | 1 | 1 | O | Q1 | $CH(CH_3)_2$ |
| 8 | Cl | F | 1 | 1 | O | Q1 | $CH_2CN$ |
| 9 | Cl | F | 1 | 1 | O | Q1 | $CH_2C_6H_5$ |
| 10 | Cl | F | 1 | 1 | O | Q1 | $CH_2CH{=}CH_2$ |
| 11 | Cl | F | 1 | 1 | O | Q1 | $CH_2OCH_3$ |
| 12 | Cl | F | 1 | 1 | O | Q1 | $CH_2CO_2C_2H_5$ |
| 13 | Cl | F | 1 | 1 | O | Q1 | $CH_2C{\equiv}CH$ |
| 14 | Cl | F | 1 | 1 | O | Q1 | $NH_2$ |
| 15 | Cl | F | 1 | 1 | O | Q1 | $CHF_2$ |
| 16 | Cl | F | 1 | 1 | O | Q1 | $CH_2CH_2CH_2F$ |
| 17 | Cl | F | 1 | 1 | O | Q1 | Na |
| 18 | Cl | F | 1 | 1 | O | Q2 | — |
| 19 | Cl | F | 1 | 1 | O | Q3 | — |
| 20 | Cl | F | 1 | 1 | O | Q4 | — |
| 21 | Cl | H | 1 | 1 | O | Q1 | $CH_3$ |
| 22 | $CF_3$ | F | 1 | 1 | O | Q1 | $CH_3$ |
| 23 | $CH_3$ | F | 1 | 1 | O | Q1 | $CH_3$ |
| 24 | CN | F | 1 | 1 | O | Q1 | $CH_3$ |
| 25 | Br | F | 1 | 1 | O | Q1 | $CH_3$ |
| 26 | F | F | 1 | 1 | O | Q1 | $CH_3$ |

TABLE 1-continued

| | | | | | | | |
|---|---|---|---|---|---|---|---|
| 27 | Cl | F | 1 | 1 | $N(CH_3)$ | Q1 | $CH_3$ |
| 28 | Cl | F | 1 | 1 | S | Q1 | $CH_3$ |
| 29 | Cl | Cl | 1 | 1 | O | Q1 | $CH_3$ |
| 30 | Cl | Cl | 1 | 1 | O | Q1 | $NH_2$ |
| 31 | Cl | Cl | 0 | 1 | O | Q1 | $CH_3$ |
| 32 | Cl | Cl | 0 | 1 | S | Q1 | $CH_3$ |
| where A is oxygen and B is sulfur: | | | | | | | |
| 33 | Cl | F | 1 | 1 | O | Q1 | H |
| 34 | Cl | F | 1 | 1 | O | Q1 | $CH_3$ |
| 35 | Cl | F | 1 | 1 | O | Q1 | $C_2H_5$ |
| 36 | Cl | F | 1 | 1 | O | Q1 | $NH_2$ |
| where A is sulfur and B is oxygen: | | | | | | | |
| 37 | Cl | F | 1 | 1 | O | Q1 | $CH_3$ |
| 38 | Cl | F | 1 | 1 | O | Q1 | $C_2H_5$ |
| 39 | Cl | F | 1 | 1 | O | Q1 | $NH_2$ |
| 40 | Cl | F | 1 | 1 | O | Q1 | $CH_2CN$ |

TABLE 2

Herbicidal(2-Substituted bicyclic heterocyclyl)-substituted heterocycles

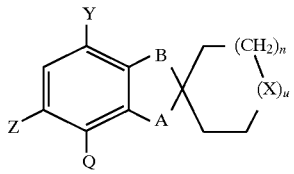

where Q is:

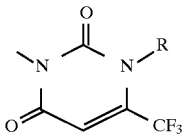

Q1 where A and B are oxygen, Y is chlorine, Z is fluorine, and R is methyl;

| Cmpd No. | $R^1$ | $R^2$ |
|---|---|---|
| 41 | $CH_3$ | methylcyclohexyl |
| 42 | $CH_3$ | 4-F-Phenylmethyl |
| 43 | $CH_3$ | $CH_2OCH_3$ |
| 44 | $CH_3$ | $CH_2SCH_3$ |
| 45 | $CH_3$ | $C_6H_5$ |
| 46 | $CH_3$ | $OCH_3$ |
| 47 | $CH_3$ | $CF_3$ |
| 48 | H | $CH_2C_6H_5$ |

TABLE 3

Characterizing Data of Representative Compounds

| Cmpd No | Melting Point (°C.)/Physical State |
|---|---|
| 1 | OIL |
| 2 | OIL |
| 3 | 165–170 |
| 4 | 220–223 |
| 41 | OIL |
| 42 | 129–141 |

Biological Testing

The heterocyclyl-spirobicyclic catechols of this invention were tested for pre- and postemergence herbicidal activity using a variety of crops and weeds. The test plants included soybean (*Glycine max* var. Winchester), field corn (*Z mays* var. Pioneer 3732), wheat (*Triticum aestivum* var. Lew), morningglory (*Ipomea lacunosa* or *Ipomea hederacea*), velvetleaf (*Abutilon theophrasti*), green foxtail (*Setaria*

*viridis*), Johnsongrass (*Sorghum halepense*), blackgrass (*Aloepecurus myosuroides*), common chickweed (*Stellaria media*), and common cocklebur (*Xanthium strumarium* L.).

For preemergence testing, two disposable fiber flats (8 cm×15 cm×25 cm) for each rate of application of each candidate herbicide were filled to an approximate depth of 6.5 cm with steam-sterilized sandy loam soil. The soil was leveled and impressed with a template to provide five evenly spaced furrows 13 cm long and 0.5 cm deep in each flat. Seeds of soybean, wheat, corn, green foxtail, and johnsongrass were planted in the furrows of the first flat, and seeds of velvetleaf, morningglory, common chickweed, cocklebur, and blackgrass were planted in the furrows of the second flat. The five-row template was employed to firmly press the seeds into place. A topping soil of equal portions of sand and sandy loam soil was placed uniformly on top of each flat to a depth of approximately 0.5 cm. Flats for postemergence testing were prepared in the same manner except that they were planted 9–14 days prior to the preemergence flats and were placed in a greenhouse and watered, thus allowing the seeds to germinate and the foliage to develop.

In both pre- and postemergence tests, a stock solution of the candidate herbicide was prepared by dissolving 0.27g of the compound in 20 mL of water/acetone (50/50) containing 0.5% v/v sorbitan monolaurate. For an application rate of 3000 g/ha of herbicide a 10 mL portion of the stock solution was diluted with water/acetone (50/50) to 45 mL. The volumes of stock solution and diluent used to prepare solutions for lower application rates are shown in the following table:

| Application Rate (g/ha) | Volume of Stock Solution (mL) | Volume of Acetone/Water (mL) | Total Volume of Spray Solution (mL) |
|---|---|---|---|
| 3000 | 10 | 35 | 45 |
| 1000 | 3 | 42 | 45 |
| 300 | 1 | 44 | 45 |
| 100 | 0.3 | 45 | 45.3 |
| 30 | 0.1 | 45 | 45.1 |
| 10 | 0.03 | 45 | 45.03 |
| 3 | 0.01 | 45 | 45.01 |

The preemergence flats were initially subjected to a light water spray. The four flats were placed two by two along a conveyor belt (i.e., the two preemergence followed by the two postemergence flats). The conveyor belt fed under a spray nozzle mounted about ten inches above the postemergent foliage. The preemergent flats were elevated on the belt so that the soil surface was at the same level below the spray nozzle as the foliage canopy of the postemergent plants. The spray of herbicidal solution was commenced and once stabilized, the flats were passed under the spray at a speed to receive a coverage equivalent of 1000L/ha. At this coverage the application rates are those shown in the above table for the individual herbicidal solutions. The preemergence flats were watered immediately thereafter, placed in the greenhouse and watered regularly at the soil surface. The postemergence flats were immediately placed in the greenhouse and not watered until 24 hours after treatment with the test solution. Thereafter they were regularly watered at ground level. After 12–17 days the plants were examined and the phytotoxicity data were recorded.

Phytotoxicity data were taken as percent control. Percent control was determined by a method similar to the 0 to 100 rating system disclosed in "Research Methods in Weed Science," 2nd ed., B. Truelove, Ed.; Southern Weed Science Society; Auburn University, Auburn, Ala., 1977. The rating system is as follows:

Herbicide Rating System

| Rating Percent Control | Description of Main Categories | Crop Description | Weed Description |
|---|---|---|---|
| 0 | No effect | No crop reduction or injury | No weed control |
| 10 | Slight effect | Slight discoloration or stunting | Very poor weed control |
| 20 | | Some discoloration, stunting or stand loss | Poor weed control |
| 30 | | Crop injury more pronounced but not lasting | Poor to deficient weed control |
| 40 | Moderate effect | Moderate injury, crop usually recovers | Deficient weed control |
| 50 | | Crop injury more lasting, recovery doubtful | Deficient to moderate weed control |
| 60 | | Lasting crop injury, no recovery | Moderate weed control |
| 70 | Severe | Heavy injury and stand loss | Control somewhat less than satisfactory |
| 80 | | Crop nearly destroyed, a few survivors | Satisfactory to good weed control |
| 90 | | Only occasional live plants left | Very good to excellent control |
| 100 | Complete effect | Complete crop destruction | Complete weed destruction |

The compounds of the present invention were tested in the laboratory as water/acetone (50/50) solutions containing 0.5% v/v sorbitan monolaurate emulsifier. It is expected that all formulations normally employed in applications of herbicides would be usable with the compounds of the present invention. These include wettable powders, emulsifiable concentrates, water suspensions, flowable concentrates, and the like.

Herbicidal activity data at selected application rates are given for various compounds of this invention in Tables 4 and 5. The test compounds are identified by numbers which correspond to those in Table 1.

TABLE 4

PREEMERGENCE HERBICIDAL ACTIVITY AT 0.3 Kg/Ha (% CONTROL)

| Cmpd No | SOY | WHT | CRN | ABUTH | IPOSS | STEME | XANPE | ALOMY | SETVI | SORHA |
|---|---|---|---|---|---|---|---|---|---|---|
| 1 | 100 | 100 | 100 | 100 | 100 | 100 | 100 | 100 | 100 | 100 |
| 2 | 100 | 70 | 100 | 100 | 100 | 100 | 100 | ND | 100 | 100 |
| 3 | 100 | 70 | 90 | 100 | 100 | 100 | 100 | ND | 100 | 95 |

TABLE 5

POSTEMERGENCE HERBICIDAL ACTIVITY AT 0.3 Kg/Ha (% CONTROL)

| Cmpd No | SOY | WHT | CRN | ABUTH | IPOSS | STEME | XANPE | ALOMY | SETVI | SORHA |
|---|---|---|---|---|---|---|---|---|---|---|
| 1 | 100 | 100 | 100 | 100 | 100 | 100 | 100 | 100 | 100 | 100 |
| 2 | 95 | 80 | 90 | 100 | 100 | 100 | 100 | ND | 100 | 100 |
| 3 | 95 | 70 | 90 | 100 | 100 | 100 | 100 | ND | 100 | 100 |

SOY is soybean, WHT is wheat, CRN is corn, ABUTH is velvetleaf, IPOSS is morningglory, STEME is chickweed, XANPE is cocklebur, ALOMY is blackgrass, SETVI is green foxtail, and SORHA is johnsongrass
ND is no data Herbicidal compositions are prepared by combining herbicidally effective amounts of the active compounds with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application. It is to be understood that the amounts specified in this specification are intended to be approximate only, as if the word "about" were placed in front of the amounts specified.

These herbicidal compositions may be applied either as water-diluted sprays, or dusts, or granules to the areas in which suppression of vegetation is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the herbicidal compound and 99.0 parts of talc.

Wettable powders, also useful formulations for both pre- and post-emergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5–80% of active ingredient, depending on the absorbency of the carrier, and usually also contain a small amount of a wetting, dispersing or emulsifying agent to facilitate dispersion. For example, a useful wettable powder formulation contains 80.0 parts of the herbicidal compound, 17.9 parts of Palmetto clay, and 1.0 part of sodium lignosulfonate and 0.3 part of sulfonated aliphatic polyester as wetting agents. Additional wetting agent and/or oil will frequently be added to the tank mix for postemergence application to facilitate dispersion on the foliage and absorption by the plant.

Other useful formulations for herbicidal applications are emulsifiable concentrates (ECs) which are homogeneous liquid compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvents. For herbicidal application these concentrates are dispersed in water or other liquid carrier and normally applied as a spray to the area to be treated. The percentage by weight of the essential active ingredient may vary according to the manner in which the composition is to be applied, but in general comprises 0.5 to 95% of active ingredient by weight of the herbicidal composition.

Flowable formulations are similar to ECs except that the active ingredient is suspended in a liquid carrier, generally water. Flowables, like ECs, may include a small amount of a surfactant, and will typically contain active ingredients in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long chain mercaptans and ethylene oxide. Many other types of useful surface-active agents are available in commerce. Surface-active agents, when used, normally comprise 1 to 15% by weight of the composition.

Other useful formulations include suspensions of the active ingredient in a relatively non-volatile solvent such as water, corn oil, kerosene, propylene glycol, or other suitable solvents.

Still other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relative coarse particles, are of particular utility for aerial distribution or for penetration of cover crop canopy. Pressurized sprays, typically aerosols wherein the active ingredient is dispersed in finely divided form as a result of vaporization of a low-boiling dispersant solvent carrier, such as the Freon fluorinated hydrocarbons, may also be used. Water-soluble or water-dispersible granules are free-flowing, non-dusty, and readily water-soluble or water-miscible. The soluble or dispersible granular formulations described in U.S. Pat. No. 3,920,442 are useful herein with the present herbicidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed. The compounds may be applied as preemergent or postemergent herbicides, with preemergent application preferred. For field use, where there are losses of herbicide, application rates may be in the range of 10 to 300 grams per hectare and are preferably in the range of 30 to 125 g/ha. The compounds of this invention are also useful as cotton defoliation and potato dessication agents. Such agents aid in the harvesting of the cotton and potato crops.

The active herbicidal compounds of the present invention may also be used in combination with other herbicides. Such herbicides include, for example: N-(phosphonomethyl) glycine, N-isopropylamine salt ("glyphosate"); aryloxyalkanoic acids such as (2,4-dichlorophenoxy)acetic acid ("2, 4-D"), (4-chloro-2-methylphenoxy)acetic acid ("MCPA"), (+/−)-2-(4chloro-2-methylphenoxy)propanoic acid ("MCPP"); ureas such as N,N-dimethyl-N'-[4-(1-methylethyl)phenyl]urea ("isoproturon"); imidazolinones such as 2-[4,5-dihydro-4-methyl-4-(1 -methylethyl)-5-oxo-1H-imidazol-2-yl]-3-pyridinecarboxylic acid ("imazapyr"), a reaction product comprising (+/−)-2-[4,5-dihydro-4-methyl-4-(1 -methylethyl)-5-oxo-1H-imidazol-2-yl]-4-methylbenzoic acid and (+/−)2-[4,5-dihydro-4-methyl-4-(1 -methylethyl)-5-oxo-1H-imidazol-2-yl]-5-methylbenzoic acid ("imazamethabenz"), (+/−)-2-[4,5-dihydro-4-methyl-4-(1 -methylethyl)-5-oxo-1H-imidazol-2-yl]-5-ethyl-3-pyridinecarboxylic acid ("imazethapyr"), and (+/−)-2-[4,5-dihydro-4-methyl-4-(1-methylethyl)-5-oxo-1H-imidazol-2-yl]-3-quinolinecarboxylic acid ("imazaquin"); diphenyl ethers such as 5-[2-chloro-4-(trifluoromethyl)phenoxy]-2-nitrobenzoic acid ("acifluorfen"), methyl 5-(2,4-dichlorophenoxy)-2-nitrobenzoate ("bifenox"), and 5-[2-chloro-4-(trifluoromethyl)phenoxy]-N-(methylsulfonyl)-2-nitrobenzamide ("fomasafen"); hydroxybenzonitriles such as 4-hydroxy-3,5-diiodobenzo-nitrile ("ioxynil") and 3,5-dibromo-4-hydroxybenzonitrile ("bromoxynil"); sulfonylureas such as 2-[[[[(4chloro-6-methoxy-2-pyrimidinyl) amino]carbonyl]amino]sulfonyl]benzoic acid ("chlorimuron"), 2-chloro-N-[[(4-methoxy-6-methyl-1,3,5-triazin-2-yl)amino]carbonyl]benzenesulfonamide ("chlorsulfuron"), 2-[[[[[(4,6-dimethoxy-2-pyrimidinyl) amino]carbonyl]amino]sufonyl]methyl]benzoic acid ("bensulfuron"), 2-[[[[(4,6-dimethoxy-2-pyrimidinyl) amino]carbonyl]-amino]sulfonyl]-1 -methy-1H-pyrazol-4-carboxylic acid ("pyrazosulfuron"), 3-[[[[(4-methoxy-6-methyl-1,3,5-triazin-2-yl)amino]carbonyl]amino]sulfonyl]-2-thiophenecarboxylic acid ("thifensulfuron"), and 2-(2-chloroethoxy)-N[[(4-methoxy-6-methyl-1,3,5-triazin-2-yl) amino]carbonyl]benzenesulfonamide ("triasulfuron"); 2-(4-aryloxyphenoxy)alkanoic acids such as (+/−)-2[4-[(6-chloro-2-benzoxazolyl)oxy]phenoxy]propanoic acid ("fenoxaprop"), (+/−)-2-[4-[[5-(trifluoromethyl)-2-pyridinyl]oxy]phenoxy]propanoic acid ("fluazifop"),(+/−)-2-[4-(6chloro-2-quinoxalinyl)oxy]phenoxy]propanoic acid ("quizalofop"), and (+/−) -2-[(2,4-dichlorophenoxy) phenoxy]propanoic acid ("diclofop"); benzothiadiazinones such as 3-(1-methylethyl)-1H-2,1,3-benzothiadiazin-4(3H)-one-2,2-dioxide ("bentazone"); 2-chloroacetanilides such as N-(butoxymethyl)-2-chloro-2',6'-diethyacetanilide ("butachlor"), 2-chloro-N-(2,6-diethylphenyl)-N-(methoxymethyl)acetamide ("alachlor"), (RS)-2-chloro-N-(2,4-dimethyl-3-thienyl)-N-(2-methoxy-1-methylethyl) acetamide ("dimethenamide"), and 2-chloro-N-(2-ethyl-6-methylphenyl)-N-(2-methoxy-1-methylethyl)acetamide ("metolachlor"); arenecarboxylic acids such as 3,6-dichloro-2-methoxybenzoic acid ("dicamba"); thiocarbamates such as S-ethyl hexahydro-1H-azepine-1 -carbothioate ("molinate"), and S-ethyl dipropylcarbamothioate ("EPTC"); dinitroanilines such as 2,6-dinitro-N,N-dipropyl-4-(trifluoromethyl)benzenamine ("trifluralin"), and N-(1-ethylpropyl)-3,4-dimethyl-2,6-dinitrobenzenamine ("pendimethalin"); triazines such as 4-amino-6-(1,1-dimethylethyl)-3-(methylthio)-1,2,4-triazin-5-one ("metribuzin"), and 6-chloro-N-ethyl-N'-(1-methylethyl)-1, 3,5-triazine-2,4-diamine ("atrazine"); bipyridyls such as 1,1'-dimethyl4,4"-bipyridinium ("paraquat"); pyridyloxyacetic acids such as [(4-amino-3,5-dichloro-6-fluoro-2-pyridinyl)oxy]acetic acid ("fluroxypyr"); and other herbicides such as (+/−)-2-[1-(ethoxyimino)butyl]-5-[2-(ethylthio)propyl]-3-hydroxy-2-cyclohexen-1-one ("sethoxydim"), (E,E)-(+/−)-2-[1-[[3-chloro-2-propenyl) oxy]imino]propyl]-5-[2-(ethylthio)propyl]-3-hydroxy-2-cyclohexen-1-one ("clethodim"), 2-[(2-chlorophenyl) methyl]-4,4-dimethyl-3-isoxazolidinone ("clomazone"), (+/−)-2-amino-4-(hydroxymethylphosphinyl)butanoic acid ("glufosinate"), N-(2,4-difluorophenyl)-2-(trifluoromethyl) phenoxy]-3-pyridinecarboxamide (diflufenican"), and 5-cyclopropylisoxazol-4-yl 2-methylsulfonyl-4-trifluoromethylphenylketone ("isoxaflutole").

It is apparent that various modifications may be made in the formulations and application of the compounds of the present invention without departing from the inventive concepts herein, as defined in the claims.

We claim:

1. A compound having the formula

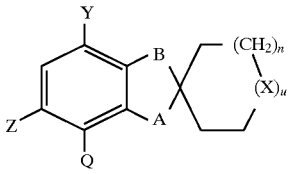

where Q is

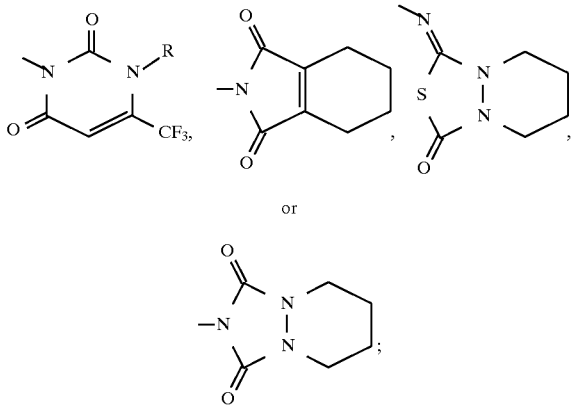

A and B are independently selected from oxygen or sulfur;

u isO or 1;

nis1to6;

Y is hydrogen, halogen, cyano, alkyl, or haloalkyl;

Z is hydrogen or halogen;

R is hydrogen, amino, straight or branched chain alkyl, haloalkyl, cyanoalkyl, alkoxyalkyl, arylalkyl, alkoxycarbonylalkyl, alkenyl, alkynyl, or a salt-forming ion; and when u is 1, X is selected from oxygen, sulfur, or -N(alkyl)-.

2. A compound of claim 1 where Q is 1-substituted-6-trifluoromethyl-2,4(1H,3H)-pyrimidinedion-3-yl.

3. A compound of claim 1 where Q is 3,4,5,6-tetrahydrophthalimid-1-yl.

4. A compound of claim 1 where Q is 2-[5,6,7,8-tetrahydro-9-oxo-1H,3H-[1,3,4]thiadiazolo[3,4-a] pyridazineiminyl].

5. A compound of claim 1 where Q is 1,6,84riazabicyclo [4.3.0]-nonane-7,9-dion-8-yl.

6. A compound of claim 1 where A and B are oxygen; Y and Z are halogen; n is 1 when u is 1 or n is 2 when u is 0; and X is oxygen.

7. A compound of claim 6 where Y is chlorine and Z is fluorine.

8. A compound of claim 7 where Q is 1-substituted-6-trifluoromethyl-2,4(1H,3H)-pyrimidinedion-3-yl or 3,4,5,6-tetrahydrophthalimid-1 -yl; and R is methyl or amino.

9. A compound of claim 8 where Q is 1-substituted-6-trifluoromethyl-2,4(1H,3H)-pyrimidinedion-3-yl.

10. A compound of claim 9 where X is oxygen and R is methyl.

11. An herbicidal composition comprising an herbicidally effective amount of a compound of claim 1, and an herbicidally compatible carrier therefor.

12. An herbicidal composition comprising an herbicidally effective amount of a compound of claim 1 and an herbicidally effective amount of one or more herbicides selected from the group consisting of glyphosate, 2,4-D, MCPA, MCPP, isoproturon, imazapyr, imazamethabenz, imazethapyr, imazaquin, acifluorfen, bifenox, fomasafen, ioxynil, bromoxynil, chlorimuron, chlorsulfuron, bensulfuron, pyrazosulfuron, thifensulfuron, triasulfuron, fenoxaprop, fluazifop, quizalofop, diclofop, bentazone, butachlor, dicamba, fluroxypyr, molinate, EPTC, trifluralin, pendimethalin, metribuzin, atrazine, paraquat, sethoxydim, clethodim, clomazone, glufosinate, diflufenican, and isoxaflutole.

13. An composition of claim 12, and an herbicidally compatible carrier therefor.

14. A method of controlling undesired plant growth, comprising application to the locus where the undesired plants are growing or are expected to grow, an herbicidally effective amount of a composition of claim 11.

15. A method of controlling undesired plant growth, comprising application to the locus where the undesired plants are growing or are expected to grow, an herbicidally effective amount of a composition of claim 13.

* * * * *